United States Patent [19]

Robin

[11] Patent Number: 4,537,961

[45] Date of Patent: Aug. 27, 1985

[54] CATALYTIC CYCLOTRIMERIZATION OF POLYISOCYANATES

[75] Inventor: Jean Robin, Lyons, France

[73] Assignee: Rhone-Poulenc Specialites Chimiques, Courbevoie, France

[21] Appl. No.: 470,988

[22] Filed: Mar. 1, 1983

[30] Foreign Application Priority Data

Mar. 4, 1982 [FR] France ................. 82 03799

[51] Int. Cl.$^3$ ..................... C07D 251/34; C08G 18/02; C08F 4/16
[52] U.S. Cl. ................................. 544/193; 544/222; 521/128; 521/902; 528/52; 526/194
[58] Field of Search ................ 544/193, 222; 521/128, 521/902; 528/52; 526/194

[56] References Cited

U.S. PATENT DOCUMENTS 3,098,048  7/1963  Shelanski et al. ............. 528/52
3,775,380  11/1973  Miller ........................... 544/193
4,412,073  10/1983  Robin ............................ 544/193

OTHER PUBLICATIONS

Kogon, J. C., J.A.C.S., vol. 78, pp. 4911–4914, Oct. 1956.

Primary Examiner—Henry R. Jiles
Assistant Examiner—J. G. Mullins
Attorney, Agent, or Firm—Burns, Doane, Swecker & Mathis

[57] ABSTRACT

Polyisocyanato-polyisocyanurates are prepared by catalytically cyclotrimerizing a polyisocyanate in the presence of a catalytically effective amount of an aminosilyl catalyst, and which is characterizing by terminating the cyclotrimerization reaction when a predetermined desired amount of isocyanurate groups has been obtained, by adding to the reaction mixture a reaction terminating amount of an organic catalyst deactivating compound comprising at least one free hydroxyl moiety, or the reaction product of such hydroxylated organic catalyst deactivating compound with an isocyanate.

11 Claims, No Drawings

CATALYTIC CYCLOTRIMERIZATION OF POLYISOCYANATES

BACKGROUND OF THE INVENTION

1. Field of the Invention

The present invention relates to the preparation of polyisocyanato-polyisocyanurates by the partial catalytic cyclotrimerization of polyisocyanates, with the reaction subsequently being deliberately terminated when the proportion of trimer reaches the desired value. This invention more especially relates to the method of deactivating the catalyst, when employing a catalyst compound comprising an aminosilyl function.

2. Description of the Prior Art

Numerous catalysts are known to this art which make it possible to cyclotrimerize aliphatic or aromatic polyisocyanates to give polyisocyanato-polyisocyanurates. Each catalyst used is subsequently deactivated by a suitable technique appropriate to the particular catalytic agent used.

It is known, for example, to carry out the partial cyclotrimerization of simple aliphatic or aromatic polyisocyanates or of polyisocyanate adducts with the aid of basic catalysts, such as tertiary amines (German Patent No. 951,168), alkali metal or alkaline earth metal derivatives, such as hydroxides, carbonates, alcoholates and the like (French Patent No. 1,190,065), quaternary ammonium hydroxides (French Patent Nos. 1,204,697 and 1,566,256; European Patent Applications Nos. 3,765 and 10,589), catalysts containing an ethyleneimine group (French Patent Nos. 1,401,513 and 2,230,642) and finally, Mannich bases generally obtained from phenol, aldehyde and secondary amine (French Patent Nos. 2,290,459 and 2,332,274). These basic catalysts are, in general, quite naturally deactivated by the introduction of an acidic compound, such as an acid (phosphoric acid, hydrochloric acid, or the like). The catalytic activity of Mannich bases can also be destroyed either by a heat treatment or by the addition of an alkylating agent (dimethyl sulfate, methyl iodide, or the like).

Furthermore, it is also known to prepare polyisocyanoto-polyisocyanurates by catalytic cyclotrimerization using phosphines as catalysts (French Patent Nos. 1,510,342 and 2,023,423; published German Patent Application No. 1,934,763). In general, the deactivation of the phosphines after the cyclotrimerization reaction is effected by the addition of an alklyating or acylating agent, or alternatively by the addition of sulfur.

Under industrial conditions, the method of terminating the catalytic cyclotrimerization reaction is of very great importance. In destroying the catalyst, the deactivator (together with the destroyed catalyst) will end up, after conversion, in the polyisocyanato-polyisocyanurate in the form of more or less complex "moieties" which, however, will unavoidably have a sometimes considerable influence on the coloration of the product, its stability, and the like.

In addition, acidic agents are corrosive towards the equipment used on the industrial scale, both for manufacture and for storage.

Furthermore, a new catalyst system has now been developed making it possible to cyclotrimerize aliphatic or cycloaliphatic polyisocyanates to give polyisocyanato-polyisocyanurates, such polyisocyanates being simple polyisocyanates or polyisocyanate adducts. Thus, the use of compounds containing aminosilyl groups as catalysts, such as monoaminosilanes, diaminosilanes, silylureas and silazanes, makes it possible to carry out the cyclotrimerization reaction without an induction period and in a uniform manner at a relatively moderate temperature, which very greatly reduces the formation of dimeric polyisocyanate. These catalysts, which will be specified in the description to follow, are described in French Patent Applications 81/02,192 and 81/23,135, assigned to the assignee hereof, and hereby expressly incorporated by reference. In these patent applications, it was indicated that the catalyst was deactivated by the addition of an acidic compound, such as a strong acid or an acid halide. It was noticed, however, that the use of these deactivators resulted in a few disadvantages (coloration, corrosion, possible catalytic effect of the corrosion products, and so forth).

SUMMARY OF THE INVENTION

Accordingly, a major object of the present invention is the provision of an improved process for the preparation of polyisocyanato-polyisocyanurates by the catalytic cyclotrimerization of polyisocyanates employing compounds containing aminosilyl groups as catalysts, which process is characterized in that, when the desired proportion of isocyanurate groups is reached, the catalyst is destroyed by the addition to the reaction medium of a deactivating compound selected from amongst organic compounds (A) bearing at least one hydroxyl group, or compounds resulting from the reaction of an isocyanate group with the organic compound (A), the organic compound (A) optionally comprising groups or atoms which are inert with respect to the isocyanate groups and being selected from among enols, alcohols, phenols, oximes and compounds bearing a hydroxysilyl group (or hydroxysilyl groups).

The use of the aforenoted deactivators provides the following advantages: inhibition of objectionable coloration, inhibition of corrosion, and the like. Depending upon the volatility of the deactivator introduced, the latter can also be completely removed after the cyclotrimerization reaction has been stopped.

The invention thus makes it possible to prepare new polyisocyanato-polyisocyanurates, and these new compounds also circumscribe another object of the present invention.

DETAILED DESCRIPTION OF THE INVENTION

More particularly according to this invention, it will be appreciated that the deactivation of the catalyst by the use of compounds bearing hydroxyl groups was totally unexpected. It is known, in fact, that the catalysts for catalytic cyclotrimerization, such as tertiary amines, alkali metal or alkaline earth metal derivatives or Mannich bases, experience an increase in the catalytic activity upon the addition of a carbamic acid ester, which acts as a co-catalyst and is usually generated directly, in situ, in the reaction medium by the addition of alcohol (which is generally secondary, but which can be primary) or phenol (compare French Patent Nos. 1,172,576, 1,304,301, 1,566,256 and 2,290,459). Furthermore, this function is also clearly demonstrated by I. C. Kogon [*Journal of the American Chemical Society*, 78, pages 4911 to 4913 (1956)] and by J. E. Kresta and H. K. Hsieh [*Makromol. Chem.*, 1978, 179 (11), 2779–82].

The deactivating agent can be an organic compound (A) bearing a hydroxyl group and selected from among enols, primary, secondary or tertiary alcohols, primary, secondary or tertiary polyols, phenols, polyphenols, oximes and compounds comprising hydroxysilyl groups, such as silanols, silanediols, siloxanes or polysiloxanes containing a hydroxysilyl group (or hydroxysilyl groups). Of course, as above mentioned, apart from the hydroxyl group, the compound (A) can optionally contain any group or atom which is inert towards the isocyanate groups, such as ester, ether or amide groups, organometallic or organometalloid groups, or the like.

β-Diketones, β-ketoesters and β-cyanoesters can be used as enol compounds having up to 10 carbon atoms. Specific examples include acetylacetone; methyl, ethyl or pentyl acetylacetate and ethyl cyanoacetate. Primary, secondary or tertiary "carbinols", generally having from 1 to 8 carbon atoms, can be used as monoalcohols. These alcohols can optionally contain substituents which are inert towards the isocyanate groups, such as ether, ester or amide groups, or the like. These alcohols can thus be hydroxyorganosilanes or hydroxyalkylsilanes. Such compounds will again be referred to in the remaining description to follow.

Advantageously, if it is desired to completely remove the remainder of the deactivator, "simple" primary or secondary monoalcohols which are purely hydrocarbon and contain only a small number of carbon atoms (at most 6 carbon atoms), such as methanol, ethanol, propanol, n-butanol, isopropanol, secondary butanol, and the like, will be used within the scope of the process of the present invention. Primary or secondary monoalcohols which have from 3 to 6 carbon atoms and whose volatility is therefore not too high, such as butanol or isopropanol, will preferably be used.

A polyol optionally substituted by one or more inert groups such as those defined above can also be used as the organic compound (A). The following are representative in this context: glycerol, propylene-1,3-glycol, butane-1,4-diol, triethylene glycol, octane-1,3-diol, butyne-1,4-diol, trimethylolpropane and diethylene glycol monoethyl or monomethyl ether (diglyme).

The polyols generally have from 2 to 12 carbon atoms and preferably from 2 to 8 carbon atoms. It will be noted, in this respect, that the use of a heavy and hence involatile deactivator, such as a polyol or a higher alcohol, makes it possible to recover the remainder of the silicon catalyst from the distillation residues, after the removal of the excess diisocyanate and the polyisocyanato-polyisocyanurate. It is thus possible, after the appropriate treatments, to recycle all the silicon introduced with the catalyst.

The phenols which can be used are monocyclic or polycyclic phenols which optionally contain one or more phenolic groups and which can contain various substituents which are inert towards the isocyanate groups, such as alkyl, ester or ether groups, halogen atoms or the like. By way of illustration, the following are exemplary of the phenols which can be used: phenol, cresols, xylenols, nonylphenol, tert.-butylphenols, dihydroxybenzene, 4,4'-dihydroxybiphenyl, 4,4'-dihydroxydiphenylmethane, hydroxynaphthalene, naphthalenediol, and the like.

The oximes which can be used include ketoximes and aldoximes obtained by reacting hydroxylamine with linear or cyclic aldehydes or ketones having at most 10 carbon atoms. Specific oximes which are exemplary are acetoneoxime, methylethylketone-oxime, cyclohexanone oxime, hexanone-2-oxime and cinnamaldehyde oxime.

By way of illustration, the following are exemplary of the compounds containing hydroxysilyl groups: trimethylsilanol, dimethylsilanediol, triethylsilanol, diethylsilanediol, triphenylsilanol, diphenylsilanediol, dihydroxydimethyldisiloxane, dihydroxydiphenyldisiloxane, bis-α,ω-dihydroxy(octaphenyltetrasiloxane), and the like.

It is obviously possible, also within the scope of the present invention, to use organosilicon compounds bearing hydroxyl groups which are not directly joined to a silicon atom. It is thus possible to use hydroxyorganosilanes or hydroxyorganopolysiloxanes such as: trimethyl-(hydroxymethyl)silane, (hydroxybutyl)-trimethylsilane, bis-(hydroxypropyl)dimethylsilane, hydroxyphenyltrimethylsilane, and the like.

The organosilicon compounds comprising hydroxyl groups are described, for example, in the text by Walter Noll entitled "Chemistry and Technology of Silicones'-'—English edition, 1968.

A compound resulting from the reaction of an isocyanate with an organic compound (A) such as defined above can also be used as the deactivating agent. It will immediately be apparent that a compound of this type is generally directly obtained, in situ, in the reaction medium still containing a very high proportion of isocyanate groups, and this takes place during the addition of the compound (A). According to a modified embodiment of the process of the invention, an alkyl or aryl urethane or alternatively an 0-silylurethane, the silyl group being directly bonded to the oxygen atom, can thus be directly introduced into the reaction medium as the deactivating agent. According to a preferred modified embodiment, a urethane derived from a compound bearing at least one isocyanate group and from a primary or secondary monoalcohol having from 1 to 8 carbon atoms is introduced as the deactivator.

Advantageously, it is preferred, within the scope of the present invention, to use a primary or secondary monoalcohol having from 3 to 6 carbon atoms. The use of butanol or isopropanol proves to be particularly suitable.

The amount of deactivating agent used can vary. It is not critical, but it will of course depend upon the amount of catalyst initially introduced into the polyisocyanate.

In general, the amount of deactivating agent is such that the molar ratio of the deactivating agent to the catalyst ranges from 0.5 to 2 and preferably ranges from 0.8 to 1.5. Advantageously, a molar ratio on the order of 1 is used.

The compound initiating the catalytic reaction can be a compound containing an aminosilyl group and having the formula (I):

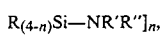

$R_{(4-n)}Si-NR'R'']_n$, in which the various symbols respectively represent the following:

R: a monovalent radical of hydrocarbon type which is aliphatic or cycloaliphatic, saturated or unsaturated and an aryl, aralkyl or alkylaryl radical, and which is optionally substituted by halogen atoms or CN groups, it being possible for two radicals R together to form a divalent hydrocarbon radical;

R': a monovalent radical selected from among the radicals R and $SiR_3$ or the amide radicals of the formula:

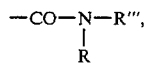

R''' representing R or SiR$_3$, with R being as defined above and it optionally being possible for the radical R', if it does not represent an amide group or a group SiR$_3$, to form a divalent hydrocarbon radical with the radical R''';

R'': a monovalent radical having the same meaning as the radical R, or a hydrogen atom if R' is not an amide radical; and n: an integer equal to 1 or 2; with the proviso that if n is equal to 2, R' is a radical R.

The catalyst, which can be an aminosilane, a diaminosilane, a silylurea or a silazane, is more preferably represented by the formula (I) in which the various symbols respectively represent the following:

R: an alkyl, alkenyl, halogenoalkyl or halogenoalkenyl radical having from 1 to 5 carbon atoms and optionally containing from 1 to 6 chlorine and/or fluorine atoms, a cycloalkyl, cycloalkenyl, halogenocycloalkyl or halogenocycloalkenyl radical having from 3 to 8 carbon atoms and optionally containing from 1 to 4 chlorine and/or fluorine atoms, an aryl, alkylaryl or halogenoaryl radical having from 6 to 8 carbon atoms and optionally containing from 1 to 4 chlorine and/or fluorine atoms, or a cyanoalkyl radical having from 3 to 4 carbon atoms;

Two symbols R borne by the same silicon atom together form a divalent radical having from 1 to 4 carbon atoms;

R': a monovalent radical selected from among the radicals R, SiR$_3$ and —CO(NR)—R''', R''' representing R, or SiR$_3$, with R being as immediately above defined, and it being possible for R' to form with R'' an alkylene radical having from 4 to 6 carbon atoms; and R'': an alkyl or alkenyl radical having from 1 to 4 carbon atoms, a cycloalkyl or cycloalkenyl radical having from 4 to 6 nuclear carbon atoms, a phenyl, tolyl or xylyl radical, or a hydrogen atom if R' is not an amide group.

The aminosilyl compounds of the formula (I) which are preferably used as cyclotrimerization catalysts are those in which the various symbols respectively represent the following:

R: a methyl, ethyl, propyl, vinyl or phenyl radical, it optionally being possible for these radicals to be chlorine-substituted and/or fluorine-substituted;

R': an alkyl radical selected from among methyl, ethyl, propyl and butyl radicals, a radical SiR$_3$, with R being as immediately above defined, or a carboxamide radical selected from among:

—CO—NR—R and —CO—NR—SiR$_3$, with R being as immediately above defined; and

R'': a methyl, ethyl, propyl or butyl radical, or a hydrogen atom.

Finally, R' and R'' can together form a butylene or pentylene radical.

Also as above mentioned, the cyclotrimerization catalyst can be an aminosilane, a diaminosilane, a monosilylurea, a disilylurea or a silazane. Given the various definitions noted hereinabove for the various radicals R, R', R'' and R''', it is easy to determine the exact chemical nature of the various compounds containing aminosilyl groups which can be used. It will be noted, in particular, that the use of a silylurea obtained by reacting a secondary amine with an N-silylated isocyanate is not envisaged. These silylureas are unsuitable in the catalytic cyclotrimerization process because they release or evolve the silylated isocyanate during heating.

The compound containing an aminosilyl group will be an aminosilant if n is equal to 1 and if R' represents a radical R, with the radicals R and R'' having one of the meanings given above, and it being possible for two radicals R to together form a divalent radical or alternatively for R' and R'' to together form a divalent radical. The following are representative of the aminosilanes: methylaminotrimethylsilane, dimethylaminotrimethylsilane, diethylaminotrimethylsilane, dibutylaminotrimethylsilane, diethylaminodimethylvinylsilane and diethylaminodimethylphenylsilane.

The compound containing an aminosilyl group will be a diaminosilane if n is equal to 2 and if R' represents the radical R, with the radicals R and R'' also having one of the meanings given above, and it being possible for two radicals R to together form a divalent radical or alternatively for R' and R'' to together form a divalent radical. The following are representative of the diaminosilanes: bis-dimethylaminodimethylsilane, bis-dimethylaminodimethylsilane, bis-dibutylaminodimethylsilane and bis-dimethylaminomethylphenylsilane.

The compound containing an aminodilyl group will be a silylurea if n is equal to 1 and R' represents the carboxamide group

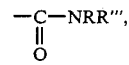

in which R''' represents a radical R or SiR$_3$, with the radicals R and R'' having one of the meanings given above, and it being possible for two radicals R to together form a divalent radical or for the two radicals R' and R'' (R' then representing R) to together form a divalent radical. The following are representative of the silylureas: N-methyl-N-trimethylsilyl-N'-methyl-N'-butylurea, N-trimethylsilyl-N-methyl-N',N'-dimethylurea, N-trimethylsilyl-N-ethyl-N',N'-dimethylurea and N-trimethylsilyl-N-butyl-N'-butyl-N'-trimethylsilylurea.

The compound containing an aminosilyl group will be a silazane if n is equal to 1 and if R' represents a group SiR$_3$.

The silazanes can be symmetrical or asymmetrical; it is preferred to use symmetrical disilazanes, with the two groups SiR$_3$ being identical.

The following are representative of the disilazanes which can be used: hexamethyldisilazane, heptamethyldisilazane, 1,3-diethyl-1,1,3,3-tetramethyldisilazane, 1,3-divinyl-1,1,3,3-tetramethyldisilazane, 1,3-diphenyl-1,1,3,3-tetramethyldisilazane, and the like.

Finally, hexamethyldisilazane and heptamethyldisilazane, which prove to be particularly advantageous catalysts, are very particularly exemplary of the disilazanes.

In the process of the present invention, any simple polyisocyanate or polyisocyanate adduct of aliphatic, cycloaliphatic or aromatic type can be cyclotrimerized to give a polyisocyanato-polyisocyanurate, provided, of course, that the compound containing an aminosilyl group which is selected as the catalyst is the appropriate one for this particular reaction.

Thus, the catalytic cyclotrimerization of simple polyisocyanates or polyisocyanate adducts in which the isocyanate groups are not directly joined to an aromatic nucleus can easily be carried out using an aminosilane, a diaminosilane, a silylurea or a silazane, such as defined above, as the catalyst.

In this respect, the following are exemplary of the aliphatic or cycloaliphatic diisocyanates: tetramethylene diisocyanate, pentamethylene diisocyanate, hexamethylene diisocyanate, 1,2-diisocyanatocyclohexane, 1,4-diisocyanatocyclohexane, 1,2-bis-(isocyanatomethyl)cyclobutane, bis-(4-isocyanatocyclohexyl)-methane and 3,3,5,-trimethyl-5-isocyanatomethyl-1-isocyanatocyclohexane.

Among these, hexamethylene diisocyanate is especially noteworthy.

Finally, among the polyisocyanate adducts or prepolymers which can be used as polyisocyanates of aliphatic type, exemplary are the modified polyisocyanates which are obtained by reacting excess aliphatic or cycloaliphatic polyisocyanate with a compound containing at least two groups which are reactive towards the isocyanate groups, such as a diamine, a diacid or the like. The modified polyisocyanates, which can be mixed with simple polyisocyanates, can contain urea, biuret, ester or siloxane groups, or the like.

Within the scope of the process of the present invention, any simple polyisocyanate or polyisocyanate adduct of aromatic type, namely, those in which the NCO grop is directly bonded to an aromatic group, can also by cyclotrimerized to give polyisocyanato-polyisocyanurate. For this purpose, the aminosilanes, the diaminosilanes or the silylureas such as defined above will be used as catalysts containing aminosilyl groups.

The following are exemplary of the aromatic diisocyanates which can be used: 1,4-diisocyanatobenzene, diisocyanatotoluenes (2,4- and 2,6-diisocyanatotoluenes or mixtures thereof), 4,4'-diisocyanatodiphenylmethane, 4,4'-diisocyanatodiphenyl ether, polymethylene and polyphenylene polyisocyanates, and the like.

The amount of catalytic agent introduced into the isocyanate can vary and typically ranges from 0.1 to 10% and preferably ranges from 0.5 to 5%, expressed by weight relative to the isocyanate used; additional small amounts of catalyst can also be introduced during the reaction, if appropriate.

The cyclotrimerization provess to give polyisocyanato-polyisocyanurate can be carried out simply by heating the reactants to a temperature which typically ranges from 50° C. to 180° C., preferably from 80° C. to 130° C. and usually is about 100° C.

It is also possible, if appropriate, to carry out the cyclotrimerization reaction in a solvent medium, it being possible for the latter to be a solvent of low polarity, such as, for example, an aliphatic or aromatic hydrocarbon, an ester or an ether. In that case, the catalyst can be introduced into the solvent and this solution can be introduced into the isocyanate. Obviously, it is also possible to introduce the catalyst solution into the isocyanate. Advantageously, the process is carried out without a solvent.

The deactivator, the type and proportion of which have been described above, is added when the proportion of isocyanurate reaches the desired value. This introduction is generally carried out at a temperature ranging from 50° C. to 180° C. and preferably ranging from 80° C. to 130° C. In a convenient procedure, the deactivator is added at the same temperature as that at which the cyclotrimerization reaction was carried out. The deactivation of the catalyst takes place very rapidly, within a few minutes.

It is then possible, if appropriate, to remove the excess monomeric polyisocyanate by any known means and to obtain a polyisocyanato-polyisocyanurate containing an excessively reduced proportion of monomeric isocyanate together with a small proportion of dimeric isocyanate.

The polyisocyanato-polyisocyanurates, such as those derived from hexamethylene diisocyanate, are well-known compounds which are of particular value as base constituents for varnish and paint, for example.

In order to further illustrate the present invention and the advantages thereof, the following specific examples are given, it being understood that same are intended only as illustrative and in nowise limitative.

EXAMPLE 1

The following material was introduced into a round-bottomed flask:

1,6-diisocyanatohexane . . . 400 g (2.38 mols).

Same was heated to 95° C. in an oil bath, 8 g (0.05 mol) of hexamethyldisilazane were added and the temperature was maintained at 100° C. for 2 hours. At this point, 1.003 isocyanate groups per 100 g were determined, namely, about 15% of the NCO groups initially present had disappeared. The reaction mixture was divided into 40 g aliquots, and the reaction was terminated by adding thereto a small amount either of a compound bearing a hydroxyl group or of a compound obtained by reacting an isocyanate group with a compound bearing a hydroxyl group.

The amount of alcohol or adduct (urethane or the like) added corresponded to one OH (or urethane) group per mol of hexamethyldisilazane.

The reaction was effectively stopped within a few minutes.

These fractions were then maintained at 100° C. for 20 hours in order to test their stability.

The reaction terminators employed were: n-butanol, isopropanol, phenol, glycerol, trimethylsilanol, the di-n-butylurethane of hexamethylene diisocyanate and the diisopropylurethane of hexamethylene diisocyanate.

In all cases, it was found that the proportion of NCO had remained virtually constant, whereas a control maintained at 100° C. for 20 hours, without the addition of a reaction terminator, underwent a large increase in viscosity, its NCO content being 0.538 NOC group/100 g after this period of time at 100° C.

EXAMPLE 2

336 g (2 mols) if diisocyanatohexane were placed in a flask. Same was heated on an oil bath to 90° to 95° C. and 4.7 g (0.04 mols) of trimethylsilydimethylamine were added. Same was maintained at 100° C. for two hours. At this point there were 1.03 isocyanate groups per 100 g.

The reaction mixture was then fractionated into 51 g portions to which were added, to stop the reaction, a small quantity of the following compounds:

hydroquinone, hydroquinone (B), cyclohexanone oxime, ethylacetylacetate, acetylacetone.

The quantity of blocking agent added corresponded to 1 OH group per mol of aminosilane with the exception of hydroquinone (B) where the amount added corresponded to 2 OH groups per mol of aminosilane.

The mixture was maintained at 100° C. for 17 hours to confirm that the reaction had truly stopped; at the end of this period of time it was found that the NCO content of the various fractions had not essentially varied (i.e., not more than 5%).

EXAMPLE 3

336 g (2 mols) of diisocyanatohexane were introduced into a flask. Same was heated on an oil bath to 95° C. and 8.7 g (0.04 mols) of N-butyl-N-trimethylsilyl-N,N'-dimethylurea were added. The mixture was maintained at 110° C. for 1 hour 20 minutes. At the end of this time 1.05 NCO groups were detected per 100 g.

The reaction mixture was fractionated into 51 g portions to which was added, to stop the reaction, the specified quantities of the following products: 1-hexanol, 1,8-octane diol, para-cresol, dimethylsilylmethanol, α,ω-dihydroxypolysiloxane (MW 1700; viscosity 50 centistokes).

The quantity was such that there resulted 1 OH group per mole of silylurea.

The various fractions were maintained at 100° C. for 20 hours and it was found that the NCO content remained practically unchanged.

EXAMPLE 4

84 g (0.5 mol) of diisocyanatohexane were introduced into a flask. Same was heated on an oil bath to 120° C. and 0.6 g (0.005 mols) of trimethylsilyldimethylamine was added. The temperature was raised to 145° C. and at the end of 1 hour, 30 minutes, 1.005 NCO groups per 100 g were determined.

0.65 g of 2-ethyl-1-hexanol (2 mols/mol of amino silane) was added to a portion of the reaction mixture and the temperature was raised to 180° C. in 15 minutes.

The mixture was maintained at 100° C. for 24 hours: the NCO content remained practically the same, while another portion of the reaction mixture, to which no ethylhexanol had been added, had become extremely viscous.

EXAMPLE 5

84 g (0.5 mols) of diisocyanatohexane were introduced into a flask. The mixture was heated on an oil bath to 100° C. and 1.6 g (0.01 mols) of hexamethyldisilazane were added. The mixture was maintained at 100° C. for two hours and then 1.00 NCO groups per 100 g were detected.

0.6 g of 1-butanol (0.8 mol per mol of silazane) was added, the mixture was divided into two portions, the first portion being maintained at 100° C. for 20 hours: the NCO content remained practically unchanged.

The second portion was cooled over 1 hour to 50° C. and was then maintained at 100° C. for 20 hours: there was no further increase in the NCO content.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims.

What is claimed is:

1. A process for the preparation of a polyisocyanato-polyisocyanurate, comprising catalytically cyclotrimerizing an aliphatic or cycloaliphatic polyisocyanate in the presence of a catalytically effective amount of an aminosilyl catalyst, and further comprising terminating the cyclotrimerization reaction when a predetermined desired amount of isocyanurate groups has been attained, by adding to the reaction mixture a reaction terminating amount of an organic catalyst deactivating compound comprising at least one free hydroxyl moiety, or the reaction product of such hydroxylated organic catalyst deactivating compound with an isocyanate.

2. The process as defined by claim 1, said hydroxylated organic catalyst deactivating compound comprising an isocyanate-inert alcohol, phenol or hydroxysilylated organosilicon moiety.

3. The process as defined by claim 1, said hydroxylated organic catalyst deactivating compound or isocyanate reaction product thereof comprising an enol, a primary, secondary or tertiary alcohol, a primary, secondary or tertiary polyol, a phenol, a polyphenol, a ketoxime, a silanol, a silanediol, a siloxane or a hydroxylated polysiloxane.

4. The process as defined by claim 3, said hydroxylated organic catalyst deactivating compound or isocyanate reaction product thereof comprising a primary or secondary monoalcohol having from 1 to 8 carbon atoms, or a urethane prepared from an isocyanate and a primary or secondary monoalcohol having from 1 to 8 carbon atoms.

5. The process as defined by claim 3, said hydroxylated organic catalyst deactivating compound comprising a primary or secondary monoalcohol having from 3 to 6 carbon atoms.

6. The process as defined by claim 1, said aminosilyl cyclotrimerization catalyst having the formula:

wherein R is an aliphatic or cycloaliphatic, saturated or unsaturated monovalent hydrocarbon radical, an aryl, aralkyl or alkylaryl radical, or a halogen or CN substituted such radical, with the proviso that any two of the radicals R may together from a single divalent hydrocarbon radical; R' is a monovalent radical R or SiR$_3$ or an amide radical having the formula:

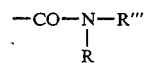

in which R''' is R or SiR$_3$, with the proviso that R', when neither an amide nor SiR$_3$, may together form with R''' a single divalent hydrocarbon radical; R'' is R, or a hydrogen atom if R' is not an amide; and n is the integer 1 or 2, with the proviso that if n is 2, R' is R.

7. The process as defined by claim 6, wherein the aminosilyl cyclotrimerization catalyst having the formula (I), R is an alkyl, alkenyl, halogenoalkyl or halogenoalkenyl radical having from 1 to 5 carbon atoms, and optionally comprising from 1 to 6 chlorine and/or fluorine substituents, a cycloalkyl, cycloalkenyl, halogenocycloalkyl or halogenocycloalkenyl radical having from 3 to 8 carbon atoms, and optionally comprising from 1 to 4 chlorine and/or fluorine substituents, an aryl, alkylaryl or halogenoaryl radical having from 6 to 8 carbon atoms, and optionally comprising from 1 to 4 chlorine and/or fluorine substituents, or a cyanoalkyl radical having from 3 to 4 carbon atoms; two of the radicals R borne by the same silicon atom together form a single divalent radical having from 1 to 4 carbon atoms; R' is R, SiR$_3$ or —CO(NR)—R''', with R''' being R or $SiR_3$, with the proviso that R' may together form with R" a single alkylene radical having from 4 to 6 carbon atoms; and R" is an alkyl or alkenyl radical having from 1 to 4 carbon atoms, a cycloalkyl or cycloalkenyl radical having from 4 to 6 nuclear carbon atoms, a phenyl, tolyl or xylyl radical, or hydrogen if R' is not an amide.

8. The process as defined by claim 6, wherein the aminosilyl cyclotrimerization catalyst is an aminosilane.

9. The process as defined by claim 6, wherein the aminosilyl cyclotrimerization catalyst is a diaminosilane.

10. The process as defined by claim 6, wherein the aminosilyl cyclotrimerization catalyst is a silylurea.

11. The process as defined by claim 6, wherein the aminosilyl cyclotrimerization catalyst is a silazane.

* * * * *